US012718832B2

(12) United States Patent
Nakamura et al.

(10) Patent No.: US 12,718,832 B2
(45) Date of Patent: Aug. 25, 2026

(54) CONTENT OUTPUT DEVICE, CONTENT OUTPUT METHOD, AND COMPUTER PROGRAM

(71) Applicant: JVCKENWOOD Corporation, Yokohama (JP)

(72) Inventors: Kodai Nakamura, Yokohama (JP); Yoshihito Kinoshita, Yokohama (JP); Junichi Kasuya, Yokohama (JP); Tomoki Sakuragi, Yokohama (JP)

(73) Assignee: JVCKENWOOD Corporation, Yokohama (JP)

( * ) Notice: Subject to any disclaimer, the term of this patent is extended or adjusted under 35 U.S.C. 154(b) by 324 days.

(21) Appl. No.: 18/295,291

(22) Filed: Apr. 4, 2023

(65) Prior Publication Data

US 2023/0245670 A1 Aug. 3, 2023

Related U.S. Application Data

(63) Continuation of application No. PCT/JP2021/037612, filed on Oct. 11, 2021.

(30) Foreign Application Priority Data

Oct. 21, 2020 (JP) ................................. 2020-176937

(51) Int. Cl.
*G10L 21/0232* (2013.01)
*A61B 5/16* (2006.01)
(Continued)

(52) U.S. Cl.
CPC ............ *G10L 21/0232* (2013.01); *A61B 5/16* (2013.01); *G06V 40/20* (2022.01); *G10L 25/63* (2013.01)

(58) Field of Classification Search
CPC ....... G10L 21/0232; G10L 25/63; A61B 5/16; A61B 5/165; G06V 40/20; H04N 5/77; H04N 5/91; H04N 5/92; H04N 23/60
(Continued)

(56) References Cited

U.S. PATENT DOCUMENTS 10,091,554 B1 * 10/2018 Newell ............ H04N 21/44218
10,832,251 B1 * 11/2020 Pike .................. G06Q 20/3224
(Continued)

FOREIGN PATENT DOCUMENTS

JP 55-500275 5/1980
JP 2005318973 * 5/2004
(Continued)

OTHER PUBLICATIONS

International Search Report and Written Opinion for International Application No. PCT/JP2021/037612 mailed on Dec. 21, 2021, 9 pages.

*Primary Examiner* — Paras D Shah
*Assistant Examiner* — Fouzia Hye Solaiman
(74) *Attorney, Agent, or Firm* — Amin, Turocy & Watson, LLP

(57) ABSTRACT

A content output device includes a content acquisition unit that acquires content, a state detection unit that detects a psychological state of a user in response to the content, a memory unit that stores psychological information indicating a psychological state when the user is in a state of tension in response to the content, an identification unit that identifies, based on information of the content and the psychological information, a cause of burden included in the content and making the user feel a psychological burden, and a conversion unit that changes an output method of the cause of burden.

6 Claims, 7 Drawing Sheets

(51) Int. Cl.
*G06V 40/20* (2022.01)
*G10L 25/63* (2013.01)

(58) Field of Classification Search
USPC .......................................................... 704/200
See application file for complete search history.

(56) References Cited

U.S. PATENT DOCUMENTS

| | | | | |
|---|---|---|---|---|
| 10,959,657 | B2 * | 3/2021 | Kaneko .................. | A61B 5/165 |
| 2005/0187437 | A1 | 8/2005 | Matsugu et al. | |
| 2005/0250996 | A1 * | 11/2005 | Shirai .................... | A61B 3/113 600/549 |
| 2008/0062291 | A1 | 3/2008 | Sako et al. | |
| 2017/0041264 | A1 * | 2/2017 | Khomami Abadi ... | A61B 5/165 |
| 2017/0162197 | A1 * | 6/2017 | Cohen ..................... | G10L 15/22 |
| 2017/0206913 | A1 * | 7/2017 | Nahman ............... | G10L 21/007 |
| 2017/0365101 | A1 * | 12/2017 | Samec .................. | G06T 19/006 |
| 2018/0114125 | A1 * | 4/2018 | Ichiboshi ............. | A61B 5/0077 |
| 2018/0279962 | A1 * | 10/2018 | Sane .................... | A61B 5/0531 |

FOREIGN PATENT DOCUMENTS

| | | | | | |
|---|---|---|---|---|---|
| JP | 2005-237561 | | | 9/2005 | |
| JP | 2008-067219 | | | 3/2008 | |
| JP | 2018-156670 | | | 10/2018 | |
| JP | 2018156670 | A | * | 10/2018 | |
| JP | 2022-068020 | | | 5/2022 | |
| KR | 20200026798 | A | * | 3/2020 | ......... G06F 16/9532 |
| WO | 79/00913 | | | 11/1979 | |

* cited by examiner

CONTENT OUTPUT DEVICE, CONTENT OUTPUT METHOD, AND COMPUTER PROGRAM

CROSS-REFERENCE TO RELATED APPLICATION

This application is a Continuation of PCT International Application No. PCT/JP2021/037612 filed on Oct. 11, 2021 which claims the benefit of priority from Japanese Patent Application No. 2020-176937 filed on Oct. 21, 2020, the entire contents of both of which are incorporated herein by reference.

BACKGROUND

1. Field of the Invention

The present disclosure relates to a content output device, a content output method, and a computer program.

2. Description of the Related Art

There are content output devices that output various types of content, such as moving images taken by themselves, moving images of meetings, movies, sports programs, and the like. As the devices that output content, there is an information processing apparatus that detects physical/mental conditions of a user, and stops presenting information or changes the information content based on a detection result of the physical/mental conditions (see, for example, Japanese Patent Application Laid-open No. 2005-237561).

However, information processing apparatuses such as those described in Japanese Patent Application Laid-open No. 2005-237561 can reduce the psychological burden of the user by stopping the presentation of information or changing the information content according to the user's psychological burden, but may not provide the necessary information.

SUMMARY

A content output device according to the present disclosure includes a content acquisition unit that acquires content, a state detection unit that detects a psychological state of a user in response to the content, a memory unit that stores psychological information indicating a psychological state when the user is in a state of tension in response to the content, an identification unit that identifies, based on information of the content and the psychological information, a cause of burden included in the content and making the user feel a psychological burden, and a conversion unit that changes an output method of the cause of burden. The state detection unit includes a behavior detection unit that detects behavior of the user in response to the content from an image and sound uttered in response to the content from a microphone, and the behavior detection unit compares the behavior and the sound with user's behavior and sound at the time of stability, and when the behavior and the sound are out of a predetermined range, determines that the user is in the state of tension.

A content output method according to the present disclosure includes acquiring content, detecting a psychological state of a user in response to the content, storing psychological information indicating a psychological state when the user is in a state of tension in response to the content, identifying, based on information of the content and the psychological information, a cause of burden included in the content and making the user feel a psychological burden, and changing an output method of the cause of burden. The detecting a psychological state of the user includes detecting behavior of the user in response to the content from an image and sound uttered in response to the content from a microphone, and the detecting behavior and sound compares the behavior and the sound with user's behavior and sound at the time of stability, and when the behavior and the sound are out of a predetermined range, determines that the user is in the state of tension.

A non-transitory computer readable recording medium storing therein a computer program according to the present disclosure causes a computer to execute acquiring content, detecting a psychological state of a user in response to the content, storing psychological information indicating a psychological state when the user is in a state of tension in response to the content, identifying, based on information of the content and the psychological information, a cause of burden included in the content and making the user feel a psychological burden, and changing an output method of the cause of burden. The detecting a psychological state of the user includes detecting behavior of the user in response to the content from an image and sound uttered in response to the content from a microphone, and the detecting behavior and sound compares the behavior and the sound with user's behavior and sound at the time of stability, and when the behavior and the sound are out of a predetermined range, determines that the user is in the state of tension.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

A detailed description of embodiments of the present disclosure will be described based on the drawings below. The present disclosure is not limited by the embodiments described below.

First Embodiment

Figure 1:
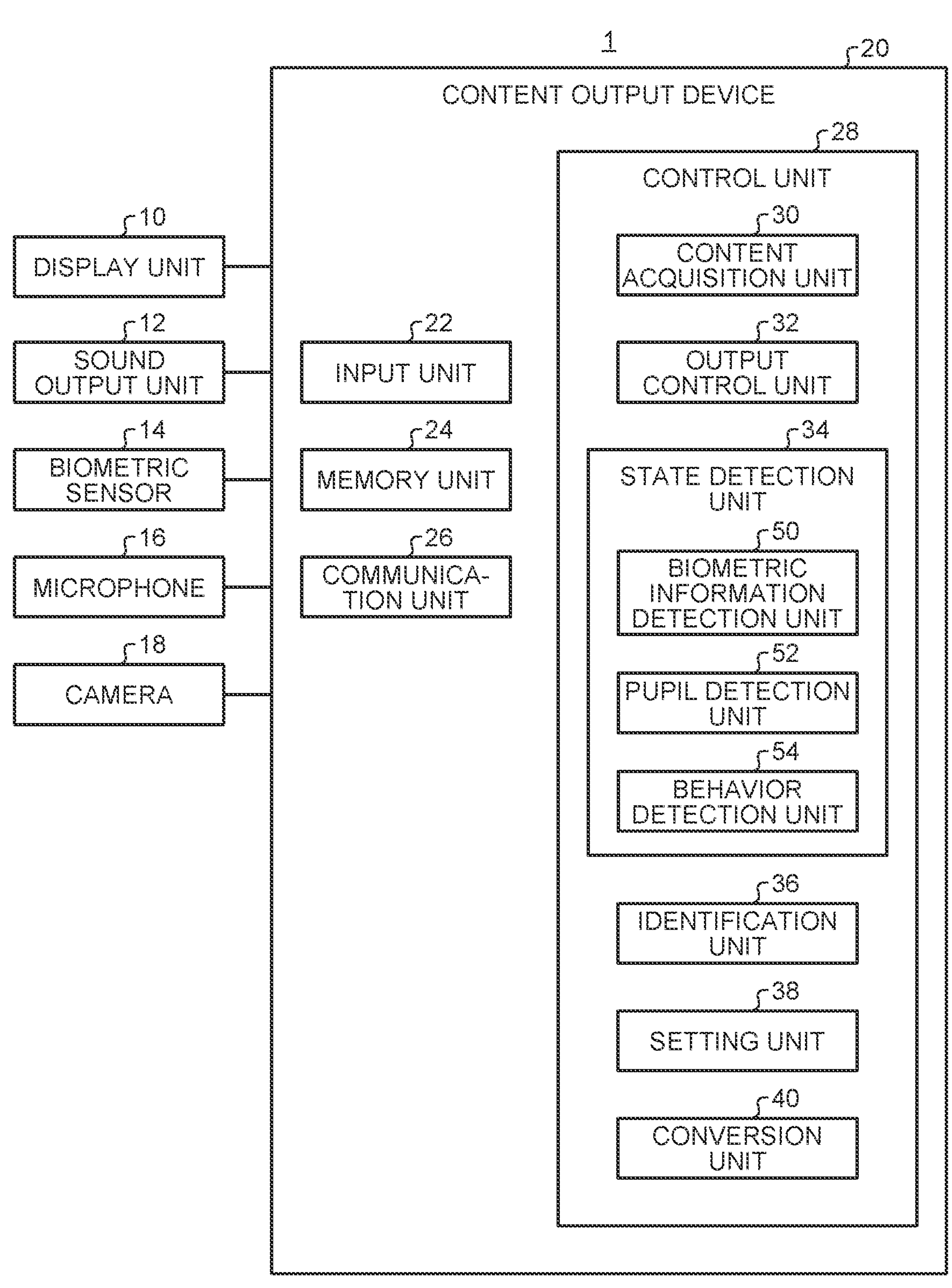
FIG. 1 is a block diagram illustrating a configuration example of a content output system according to a first embodiment.

A content output system according to a first embodiment will be described by using FIG. 1. FIG. 1 is a block diagram illustrating a configuration example of the content output system according to the first embodiment.

As illustrated in FIG. 1, a content output system 1 is provided with a display unit 10, a sound output unit 12, a biometric sensor 14, a microphone 16, a camera 18, and a content output device 20. In a case in which the content output system 1 determines that a user feels a psychological burden for content that includes videos and music, the content output system 1 performs conversion processing on the content to reduce the psychological burden felt by the user and outputs the content.

The display unit 10 displays various types of videos. The display unit 10 displays, for example, movies and TV programs. The display unit 10 can be implemented with a display including, for example, a liquid crystal display or an organic electro-luminescence (EL) display.

The sound output unit 12 outputs various types of sounds. The sound output unit 12 outputs, for example, a sound related to the video displayed on the display unit 10. The sound output unit 12 can be implemented with, for example, a speaker. The sound output unit 12 may be, for example, headphones worn on the user's head.

The biometric sensor 14 detects various pieces of biometric information of the user. The biometric sensor 14 may be composed of various sensors that detect biometric information. The biometric information may include, for example, but is not limited to, information related to heart rate, blood flow, blood pressure, body temperature, and brain waves. The biometric sensor 14 can be implemented with, for example, a wearable device worn by the user. Examples of the wearable device include, but are not limited to, smart watches.

The microphone 16 detects ambient sound. The microphone 16 detects, for example, a sound emitted from a user viewing the video displayed on the display unit 10. The microphone 16 can be implemented with, for example, a well-known microphone.

The camera 18 is an imaging device that images an image of the user. The camera 18 images, for example, the user viewing the video displayed on the display unit 10. The camera 18 images, for example, pupils of the user viewing the video displayed on the display unit 10. The camera 18 can be implemented with, for example, a camera including a charge coupled device (CCD) or complementary metal-oxide semiconductor (CMOS) sensor.

The display unit 10, the sound output unit 12, the biometric sensor 14, the microphone 16, and the camera 18 may be integrally constituted as, for example, a head mounted display (HMD) worn on the user's head.

The content output device 20 is provided with an input unit 22, a memory unit 24, a communication unit 26, and a control unit 28.

The input unit 22 is an input device for inputting various operations to the content output device 20. The input unit 22 receives various operations from the user. The input unit 22 is implemented with, for example, buttons, switches, touch panels, and the like.

The memory unit 24 is a memory that stores various types of information. The memory unit 24 stores information such as, for example, arithmetic operation content of the control unit 28 and computer programs. The memory unit 24 stores, for example, content information related to content that is output from the display unit 10 and the sound output unit 12. The content may include, for example, information related to various movies, TV programs, music, and the like. The content may include moving images taken by the user and music recorded by the user. The content may include the user's own video and the user's own sound. The memory unit 24 stores, for example, biometric information of the user who may use the content output system 1. The biometric information may include psychological information on heart rate, blood flow, blood pressure, body temperature, brain waves, pupil state, behavior, and sound when the user is in a state of tension. The state of tension implies that the user feels the psychological burden above a predetermined level. The memory unit 24 includes, for example, at least one of main memory devices such as random access memory (RAM), read only memory (ROM), and an external memory device such as hard disk drive (HDD).

The communication unit 26 is a communication device that transmits and receives content information between the content output device 20 and an external device. The external device is, for example, a server device that distributes content such as movies, TV programs, and music. The content information acquired by the communication unit 26 is stored in the memory unit 24.

The control unit 28 controls an operation of each unit of the content output device 20. The control unit 28 is implemented with, for example, central processing unit (CPU) or micro processing unit (MPU), which executes a computer program stored in the memory unit 24 or the like using RAM or the like as a work area. The control unit 28 may be implemented with an integrated circuit such as application specific integrated circuit (ASIC), field programmable gate array (FPGA), and the like, for example. The control unit 28 may be implemented with a combination of hardware and software.

The control unit 28 is provided with a content acquisition unit 30, an output control unit 32, a state detection unit 34, an identification unit 36, a setting unit 38, and a conversion unit 40.

The content acquisition unit 30 acquires various types of content. The content acquisition unit 30 acquires, for example, content stored in the memory unit 24. The content can include at least one of video or sound.

The output control unit 32 outputs the content acquired by the content acquisition unit 30. The output control unit 32 displays, on the display unit 10, content related to video, which is acquired by the content acquisition unit 30, for example. The output control unit 32 causes, for example, the sound output unit 12 to output content related to a sound acquired by the content acquisition unit 30.

The state detection unit 34 detects the psychological state of the user in response to the content output by the output control unit 32. The state detection unit 34 determines, for example, the psychological state of the user, such as whether the user is in a state of tension, based on a detection result of the user obtained by at least one of the biometric sensor 14, the microphone 16, and the camera 18 and the biometric information of the user stored in the memory unit 24. The state detection unit 34 is provided with a biometric information detection unit 50, a pupil detection unit 52, and a behavior detection unit 54.

The biometric information detection unit 50 acquires biometric information of the user from the biometric sensor 14 in response to the content output by the output control unit 32. The biometric information detection unit 50 detects the psychological state of the user based on biometric information such as the user's heart rate, blood flow, blood pressure, body temperature, and brain waves. The biometric information detection unit 50 compares, for example, the user's heart rate information acquired by the biometric sensor 14 with the user's heart rate information at stability stored in the memory unit 24, and determines that the user is in a state of tension in a case in which the compared result is out of a predetermined range.

The pupil detection unit 52 acquires a face image of the user's face from the camera 18 in response to the content output by the output control unit 32. The pupil detection unit 52 detects a state of the user's pupils based on the face image of the user. The pupil detection unit 52 detects the psychological state of the user based on the state of the user's pupils. The pupil detection unit 52 compares, for example, the detected state of the user's pupil with pupil information of the user at stability, which is stored in the memory unit 24, and determines that the user is in a state of tension in a case in which the compared result is out of a predetermined range.

The behavior detection unit 54 acquires an image of the user's behavior from the camera 18 in response to the content output by the output control unit 32. The behavior detection unit 54 acquires, from the microphone 16, the sound uttered by the user in response to the content output by the output control unit 32. The behavior detection unit 54 detects the psychological state of the user based on the behavior of the user. The behavior detection unit 54 detects the psychological state of the user based on the sound uttered by the user. The behavior detection unit 54 may acquire at least one of the user's behavior or the sound uttered by the user in response to the content output by the output control unit 32. The behavior detection unit 54 compares at least one of the user's behavior acquired by the camera 18 or the user's sound acquired by the microphone 16 with information related to the user's behavior or sound at the time of stability stored in the memory unit 24, and determines that the user is in a state of tension in a case in which both or either the user's behavior and sound are out of a predetermined range.

The state detection unit 34 may, for example, assign weights to the detection results of the psychological state of the user to determine whether the psychological state is tense. Specifically, the state detection unit 34 may determine whether the psychological state of the user is tense by assigning different weights to determination results respectively obtained via the biometric information detection unit 50, the pupil detection unit 52, and the behavior detection unit 54. The measure, method, and the like of weighting may be modified according to the user. For example, the state detection unit 34 may determine whether the psychological state of the user is tense by giving greater weight to a pulse rate measurement for a user who tends to have a faster pulse rate during a state of tension.

The identification unit 36 identifies a cause of burden, which makes the user be in a state of tension in a case in which it is determined that the user is being in a state of tension by the state detection unit 34. The identification unit 36 identifies, for example, a cause of burden, which makes the user be in a state of tension based on the content output by the output control unit 32 in a case in which it is determined that the user is being in a state of tension by the state detection unit 34. For example, in a case in which people included in the content output by the output control unit 32, the identification unit 36 identifies a specific person who makes the user feel the psychological burden, among the people included in the content.

The setting unit 38 sets a flag in response to the content acquired by the content acquisition unit 30. The setting unit 38 sets, for example, a burden flag indicating that a psychological burden of the user is high with respect to a part of the content, which is identified by the identification unit 36 and includes the cause of burden, which makes the user be in a state of tension.

The conversion unit 40 converts content. The conversion unit 40 changes the information of the content and an output method of the specified person identified by the identification unit 36. The conversion unit 40, for example, converts the content based on the burden flag set by the setting unit 38. The conversion unit 40 cancels, for example, a sound of the factor, which is included in a part to which the burden flag is set and makes the user feel the psychological burden, or converts the sound that makes the user feel the psychological burden to another sound.

Burden Flag Setting Processing

Figure 2:
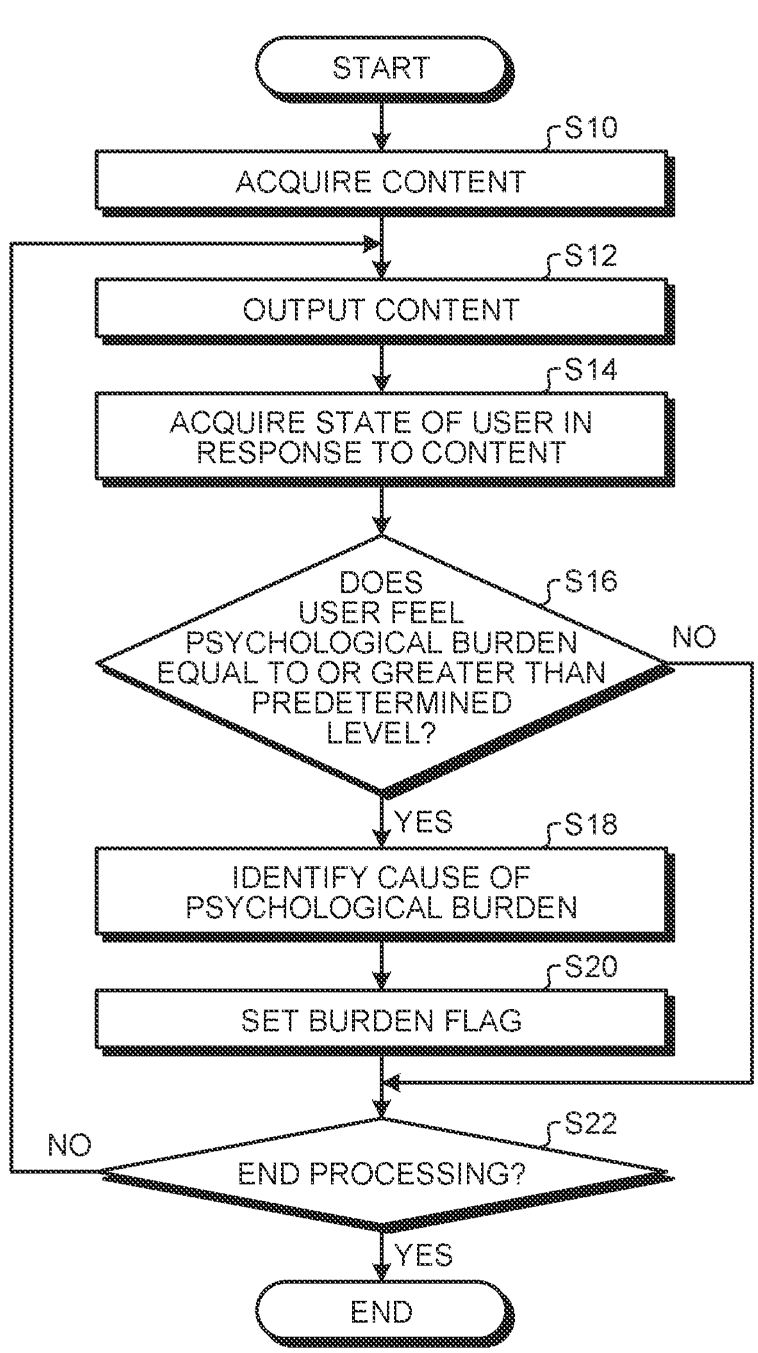
FIG. 2 is a flowchart illustrating an example of a processing flow for setting a burden flag according to the first embodiment.

A processing flow for setting the burden flag according to the first embodiment will be described by using FIG. 2. FIG. 2 is a flowchart illustrating an example of the processing flow for setting the burden flag according to the first embodiment.

The content acquisition unit 30 acquires content (step S10). Specifically, the content acquisition unit 30 outputs, for example, content including at least one of a video or a sound stored in the memory unit 24. Next, the processing proceeds to step S12.

The output control unit 32 outputs the content (step S12). Specifically, the output control unit 32 outputs content from at least one of the display unit 10 or the sound output unit 12 according to the content acquired by the content acquisition unit 30. Next, the processing proceeds to step S14.

The state detection unit 34 acquires a state of the user in response to the content (step S14). For example, the biometric information detection unit 50 of the state detection unit 34 acquires biometric information of the user in response to the content from the biometric sensor 14. For example, the pupil detection unit 52 of the state detection unit 34 acquires pupil information of the user in response to the content from the camera 18. For example, the behavior detection unit 54 of the state detection unit 34 acquires a sound uttered by the user in response to the content from the microphone 16. For example, the behavior detection unit 54 of the state detection unit 34 acquires behavior information on the user's behavior in response to the content from the camera 18. For example, the state detection unit 34 may acquire all of the biometric information, the pupil information, and the behavior information, or at least one of the biometric information, the pupil information, or the behavior information. Next, the processing proceeds to step S16.

The state detection unit 34 determines whether the user feels a psychological burden equal to or greater than a predetermined level (step S16). Specifically, the state detection unit 34 determines whether the user feels a psychological burden equal to or greater than a predetermined level in response to the content based on the biometric information of the user acquired at step S14. For example, the state detection unit 34 determines whether the user feels a psychological burden equal to or greater than a predetermined level based on at least one of the biometric information, the pupil information, and the behavior information of the user acquired at step S14, and the biometric information, the pupil information, and the behavior information, which are indicated when the user is in a state of tension stored in the memory unit 24. In a case in which it is determined that the user feels a psychological burden equal to or greater than the predetermined level (Yes at step S16), the processing proceeds to step S18. In a case in which it is determined that the user does not feel a psychological burden equal to or greater than the predetermined level (No at step S16), the processing proceeds to step S22.

In a case in which it is determined as Yes at step S16, the identification unit 36 identifies a cause of burden that makes the user feel the psychological burden (step S18). Specifically, the identification unit 36 performs analysis processing on the content, extracts various subjects included in the content, and identifies the cause of burden based on the extracted subjects. For example, the identification unit 36 performs the analysis processing on the content and detects to include tense or yelling sounds, thereby identifying a specific person who may be a cause of the user's psychological burden. For example, the identification unit 36 performs the analysis processing on the content and detects that a person with a strong or yelling facial expression is speaking, thereby identifying a specific person who may be a cause of the user's psychological burden. For example, in a case in which the identification unit 36 performs the analysis processing on the content, and as a result, the content is a video, the identification unit 36 identifies a speaker based on a direction of a line of sight of a person included in the video and a mouth movement of the person, and detects content of a speech, thereby identifying a specific person who may be a cause of the user's psychological burden. The identification unit 36 may identify, for example, unpleasant sound as a cause of burden. Next, the processing proceeds to step S20.

The setting unit 38 sets a burden flag in response to the content (step S20). Specifically, the setting unit 38 sets a burden flag with respect to a part where the user feels the psychological burden, which is identified by the identification unit 36. For example, the setting unit 38 sets a burden flag with respect to an utterance from a specific person, which may make the user feel the psychological burden, and identified by the identification unit 36. Next, the processing proceeds to step S22.

Figure 3:
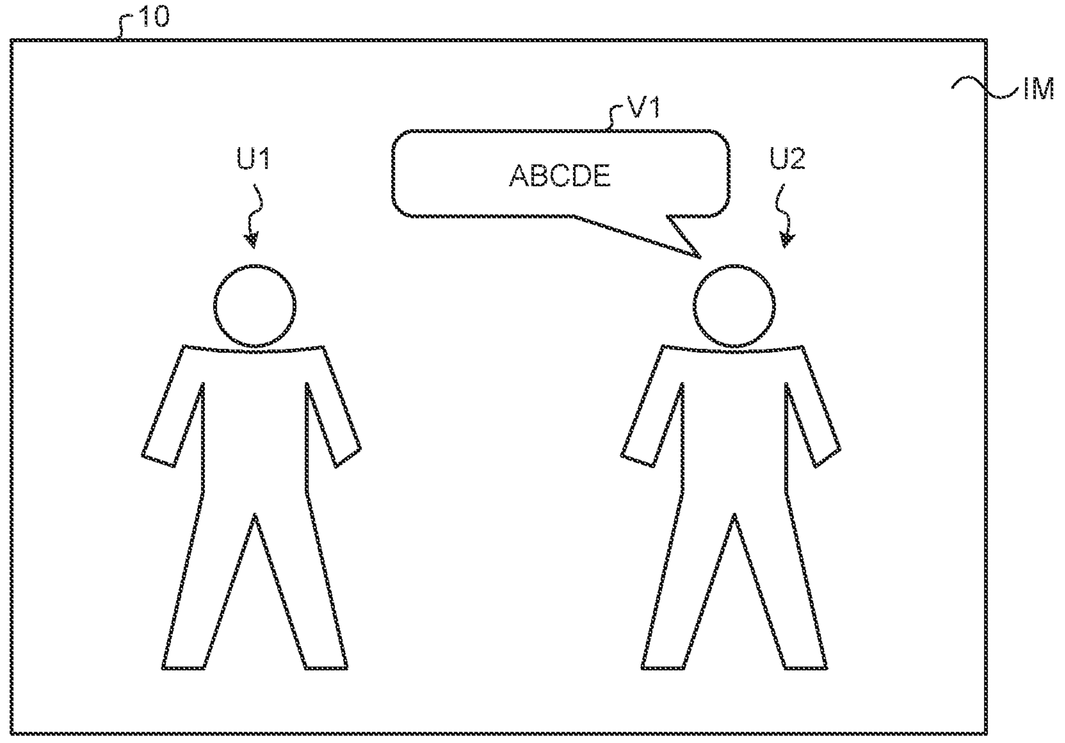
FIG. 3 is a diagram illustrating a method of setting the burden flag with respect to content.

Here, a method of setting the burden flag with respect to the content will be described by using FIG. 3. FIG. 3 is a diagram illustrating the method of setting the burden flag with respect to the content. FIG. 3 illustrates a video IM displayed on the display unit 10 as the content. As illustrated in FIG. 3, the video IM includes a person U1 and a person U2. In this case, the identification unit 36 identifies a person who is speaking based on a direction of a line of sight and a mouth movement of each of the person U1 and the person U2. In the example illustrated in FIG. 3, an utterance V1 of the person U2 is illustrated conceptually, such as "ABCDE", but in a practical sense, specific content of the utterance is identified. The identification unit 36 identifies the utterance V1 as a cause of the psychological burden felt by the user viewing the video IM. In this case, the setting unit 38 sets a burden flag with respect to the utterance V1. In other words, the identification unit 36 identifies the person U2 as a specific person who is causing the user to feel the psychological burden. The setting unit 38 sets a burden flag on the utterance V1 from the person U2 who is the specific person making the user feel the psychological burden.

Return to FIG. 2. The control unit 28 determines whether to end the processing (step S22). For example, the control unit 28 determines that the processing ends in a case in which the content output is complete. For example, the control unit 28 determines that the processing ends in a case in which an operation to terminate the content output is received, or a case in which an operation to turn off the power of the content output device 20 is received. In a case in which it is determined that the processing ends (Yes at step S22), the processing in FIG. 2 ends. In a case in which it is determined that the processing is in progress (No at step S22), the processing proceeds to step S12, and the above-described processing is repeated.

Content Conversion Processing

Figure 4:
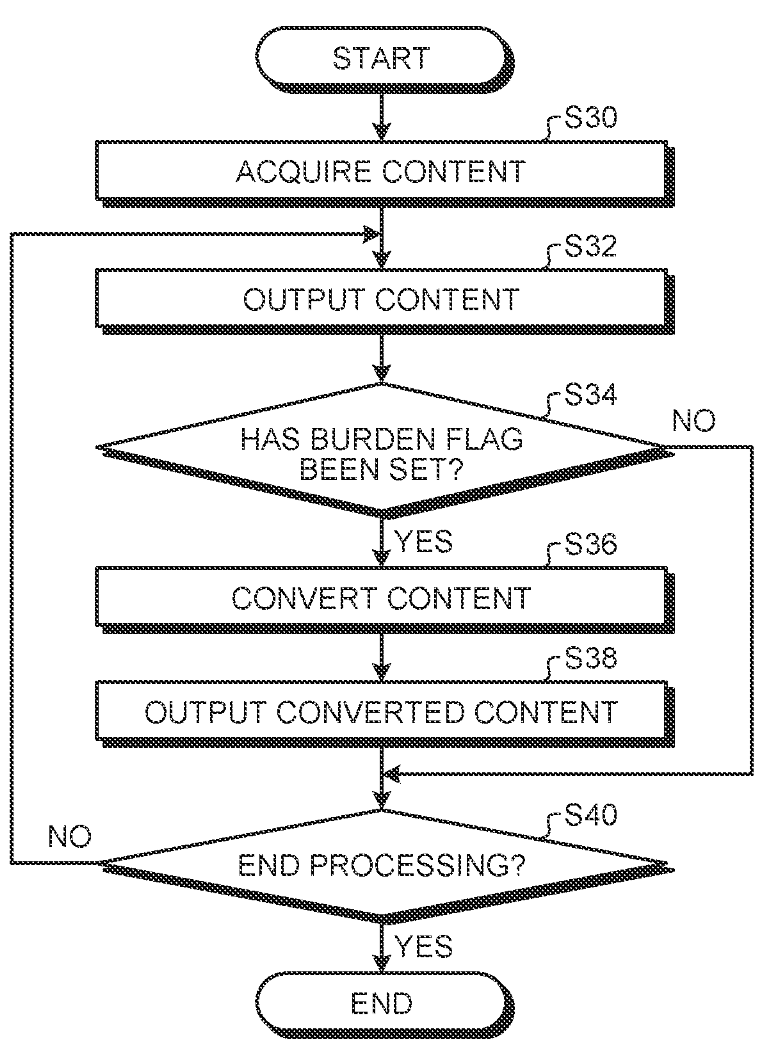
FIG. 4 is a flowchart illustrating an example of a processing flow for converting and outputting the content according to the first embodiment.

A processing flow for converting and outputting the content according to the first embodiment will be described by using FIG. 4. FIG. 4 is a flowchart illustrating an example of the processing flow for converting and outputting the content according to the first embodiment.

The processing in step S30 and the processing in step S32 are identical to those in step S10 and step S12 illustrated in FIG. 2, respectively. Thus, the descriptions will not be repeated.

After step S32, the conversion unit 40 determines whether the burden flag has been set in the content to be output by the output control unit 32 (step S34). Specifically, the conversion unit 40 analyzes the content to determine whether the burden flag set by the setting unit 38 has been set. In a case in which it is determined that the burden flag has been set (Yes at step S34), the processing proceeds to step S36. In a case in which it is determined that the burden flag has not been set (No at step S34), the processing proceeds to step S40.

In a case in which it is determined as Yes at step S34, the conversion unit 40 converts the content (step S36). The conversion unit 40 executes conversion processing on a part of the content output by the output control unit 32, in which the burden flag is set by the setting unit 38. Specifically, the conversion unit 40 executes the conversion processing on a part the content in which the burden flag is set by the setting unit 38 so that the user does not feel the psychological burden in response to the content.

Figure 5:
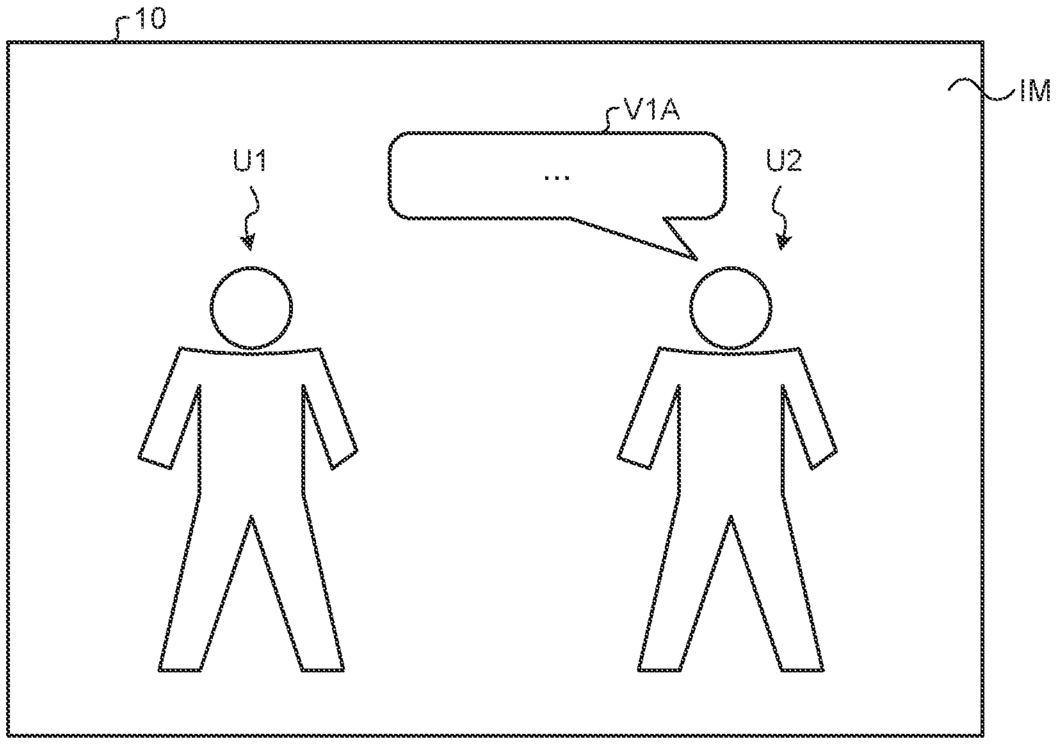
FIG. 5 is a diagram illustrating a method of converting content.

A method of converting the content will be described by using FIG. 5. FIG. 5 is a diagram illustrating the method of converting the content. FIG. 5 illustrates the video IM that includes the person U1 and the person U2 illustrated in FIG. 3. In the example illustrated in FIG. 5, the conversion unit 40 detects that the burden flag has been set in the utterance V1 of the person U2 in the video IM, as illustrated in FIG. 3. The conversion unit 40 executes, for example, the conversion processing on the utterance V1 of the person U2 to convert the utterance V1 into an utterance V1A. For example, the conversion unit 40 executes the conversion processing on the utterance V1 such as "ABCDE" to convert the utterance V1 into the utterance V1A such as " . . . ". Specifically, the conversion unit 40 executes muting processing on the utterance of the person U2. In other words, the conversion unit 40 mutes the utterance V1 of the person U2, which has made the user feel the psychological burden. The conversion unit 40, for example, mutes the utterance V1 of the person U by outputting, from the sound output unit 12, a sound in the opposite phase of the sound of the person U2 who has made the user feel the psychological burden. The conversion unit 40 may convert the utterance V1 of the person U2 into a sound of another person by changing a frequency of the sound output from the sound output unit 12. For example, the conversion unit 40 may convert the sound of the person U2 to that of a favorite celebrity or other sound. The conversion unit 40 may also convert the utterance V1 of the person U2 to other sounds that make the user does not feel the psychological burden.

Return to FIG. 4. The output control unit 32 outputs the content that has been converted by the conversion unit 40 (step S38). In other words, the output control unit 32 outputs the converted content in such a way that the user does not feel the psychological burden.

The processing at step S40 is identical to the processing at step S22 illustrated in FIG. 2. Thus, the description will not be repeated.

As described above, the first embodiment executes the content conversion processing on the content for which the user has felt the psychological burden in the past so that the user will not feel the psychological burden in a case in which the user views the content again. According to this, the first embodiment enables necessary information to be presented while reducing the psychological burden of the user.

Second Embodiment

Figure 6:
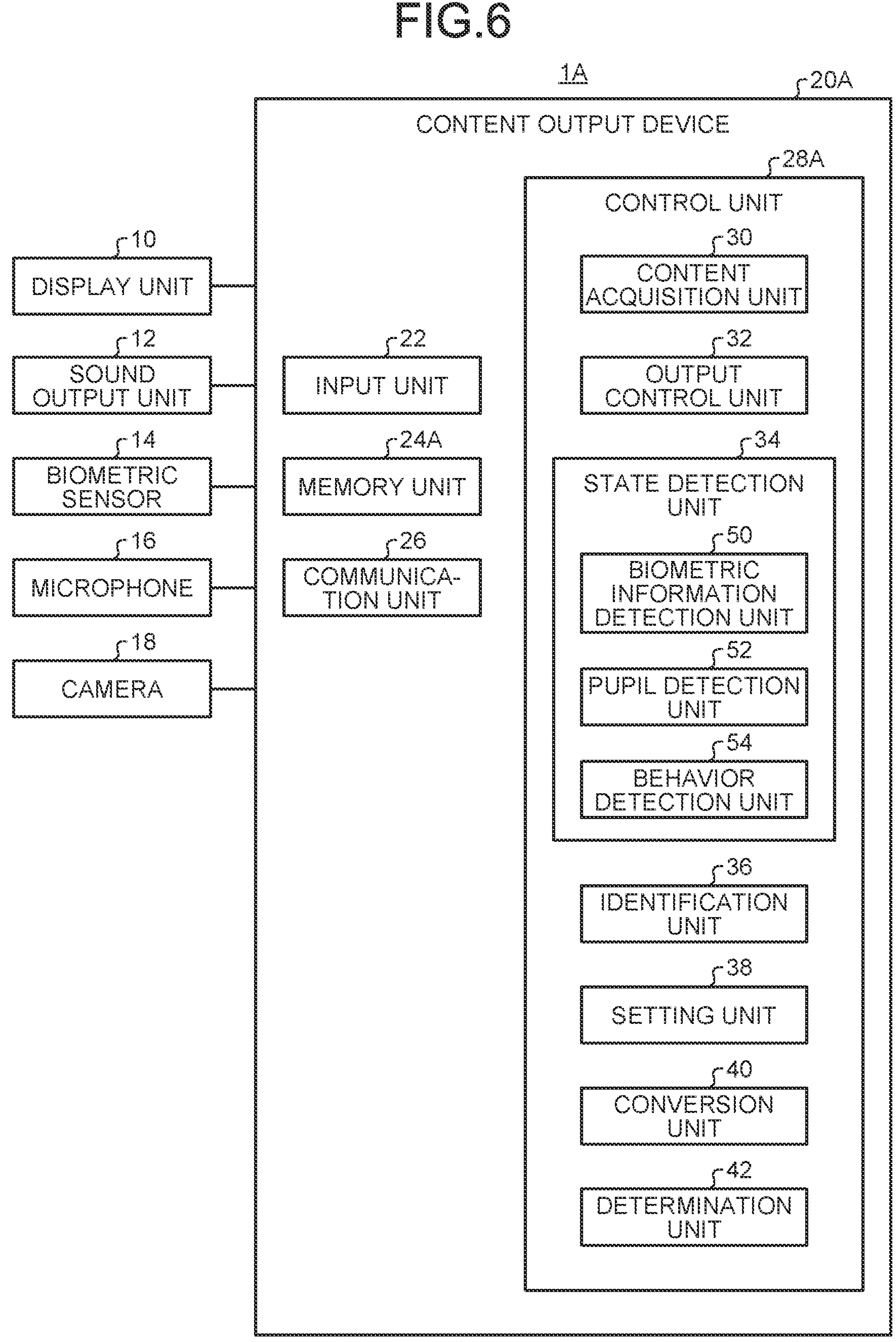
FIG. 6 is a block diagram illustrating a configuration example of a content output system according to a second embodiment.

Next, a second embodiment will be described. FIG. 6 is a block diagram illustrating a configuration example of a content output system according to the second embodiment. As illustrated in FIG. 6, a content output system 1A differs from the content output system 1 illustrated in FIG. 1 in that a control unit 28A of a content output device 20A is provided with a determination unit 42.

In the second embodiment, TV programs and other programs being broadcast in real-time are acquired as content, and whether the user feels a psychological burden while viewing the TV programs is determined. In the second embodiment, in a case in which it is determined that the user feels the psychological burden, the conversion processing is performed on the content being broadcast in real-time, and then the converted content is output.

A memory unit 24A associates the biometric information when the user is being in a state of tension with scenes, music, utterances, and the like in content that makes the user feel a state of tension, and stores the association results. In other words, the memory unit 24A stores information related to scenes, music, utterances, and the like in content, which are assumed to make the user feel the psychological burden equal to or greater than a predetermined level, as burden information.

The determination unit 42 determines a psychological state of the user. The determination unit 42 determines, for example, whether the user feels a psychological burden equal to or greater than a predetermined level in response to the content acquired by the content acquisition unit 30.

Content Conversion Processing

Figure 7:
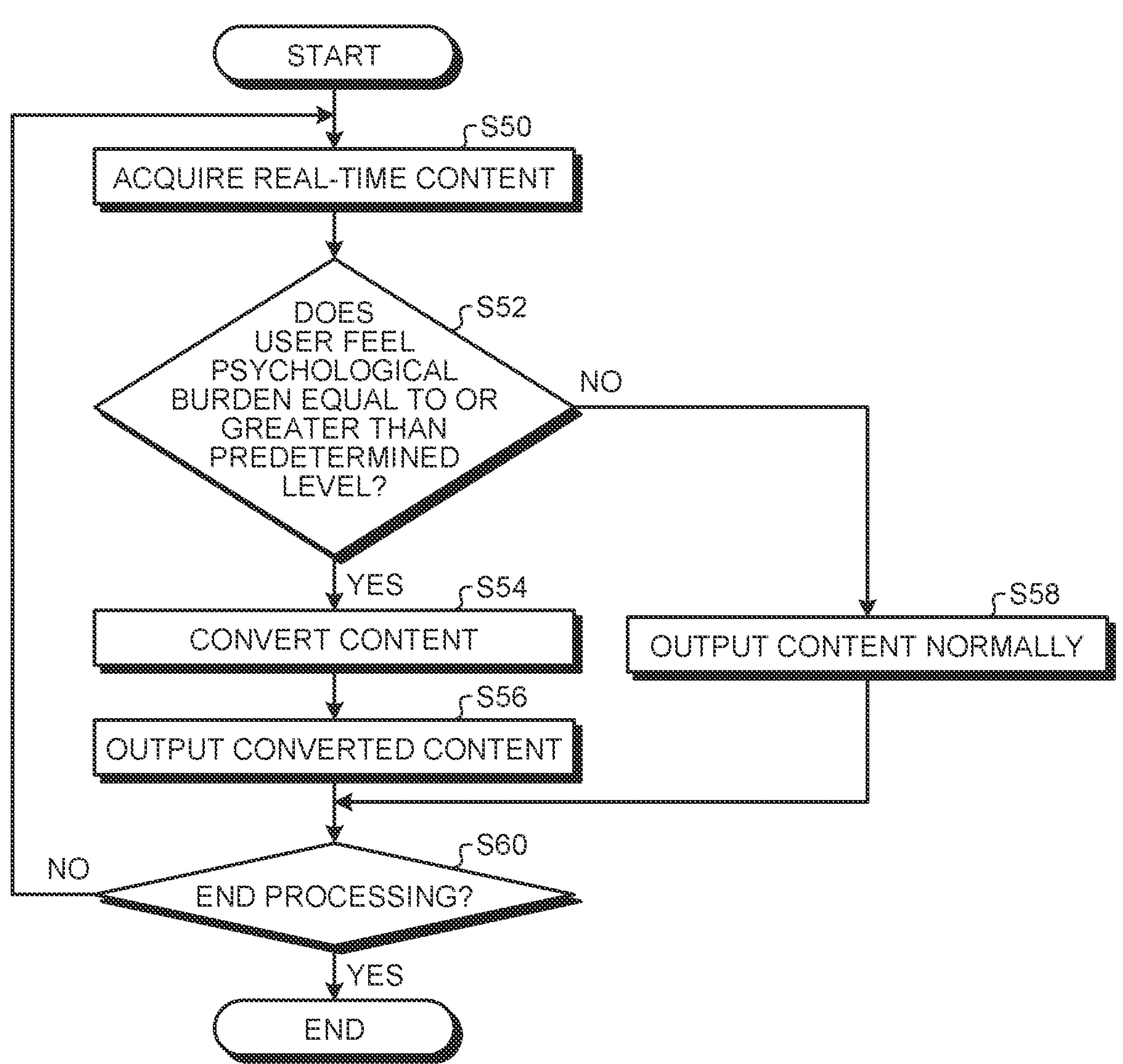
FIG. 7 is a flowchart illustrating an example of a processing flow for converting content according to the second embodiment.

The content conversion processing according to the second embodiment will be described by using FIG. 7. FIG. 7 is a flowchart illustrating an example of a processing flow for converting content according to the second embodiment.

The content acquisition unit 30 acquires real-time content (step S50). Specifically, the content acquisition unit 30 acquires, for example, video such as TV programs being broadcast in real-time via the communication unit 26. Next, the processing proceeds to step S52.

The determination unit 42 determines whether the user feels a psychological burden equal to or greater than a predetermined level in response to the content acquired by the content acquisition unit 30 (step S52). Specifically, the determination unit 42 determines, based on the burden information stored by the memory unit 24A, whether the content acquired by the content acquisition unit 30 includes scenes, music, utterances and the like, which are assumed to make the user feel the psychological burden. In a case in which it is determined that the user feels a psychological burden equal to or greater than a predetermined level (Yes at step S52), the user proceeds to step S54. In a case in which it is determined that the user does not feel a psychological burden equal to or greater than the predetermined level (No at step S52), the processing proceeds to step S58.

In a case in which it is determined as Yes at step S52, the conversion unit 40 converts the content (step S54). The conversion unit 40 executes the conversion processing so that the user does not feel the psychological burden in response to a part of the content acquired by the content acquisition unit 30, which is assumed to make the user feel a psychological burden equal to or greater than a predetermined level. Next, the processing proceeds to step S56.

The output control unit 32 outputs the content that has been converted by the conversion unit 40 (step S56). That is, the output control unit 32 outputs the converted real-time content in such a way that the user does not feel the psychological burden. Next, the processing proceeds to step S60.

In a case in which it is determined as No at step S52, the output control unit 32 outputs the content normally (step S58). Specifically, the output control unit 32 outputs content from at least one of the display unit 10 or the sound output unit 12 according to the content acquired by the content acquisition unit 30. Next, the processing proceeds to step S60.

The processing at step S60 is identical to the processing at step S22 illustrated in FIG. 2. Thus, the description will not be repeated.

As described above, in the second embodiment, the conversion processing is executed on the content acquired in real-time, for which the user has felt the psychological burden in the past, in such a way that the user does not feel the psychological burden. According to this, in the second embodiment, the psychological burden of the user in response to TV programs and other content, which are being broadcast in real-time, can be reduced.

In each of the embodiments described above, the case in which the conversion processing is performed on the sound that makes the user feel the psychological burden is described, but the present disclosure is not limited thereto. For example, the present disclosure may be applied to a case in which the conversion processing is performed on a video to reduce a psychological burden of the user in a case in which it is determined that the user feel the psychological burden in response to the video. In this case, for example, mosaicking, blurring, and changing a color of an area of a video where the user feels a psychological burden may be performed on the video that makes the user feel the psychological burden.

The present disclosure is effective in that necessary information can be presented while reducing the psychological burden on the user.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A content output device comprising:

a camera that captures an image of a user;

a microphone that detects ambient sound including sound emitted from the user;

a memory that is configured to store computer-executable instructions;

a biometric sensor configured to detect biometric information including at least one of heart rate, blood flow, blood pressure, body temperature, or brain waves; and a processor that is configured to execute the computer-executable instructions to perform operations, the operations comprising:

acquiring content;

outputting the content as at least video output via a display unit and audio output via a sound output unit;

detecting a psychological state of the user in response to the content based on the biometric information;

storing, in the memory, psychological information indicating a psychological state when the user is in a state of tension in response to the content;

performing analysis processing on the content to identify, based on information on at least one of a sound of a person detected in the audio output by the analysis processing or a facial expression of the person detected in the video output by the analysis processing and the psychological information, a cause of burden included in the content and making the user feel a psychological burden; and modifying the content in a manner that changes an output method of the cause of burden, wherein the detecting further comprises detecting, based on analysis of the image, behavior of the user in response to the content, and sound, detected by the microphone, uttered by the user in response to the content, the detecting of the behavior further comprises comparing the behavior of the user in response to the content and the sound uttered by the user in response to the content with the user's behavior and sound at a time of stability, and in response to determining that the behavior of the user in response to the content and the sound uttered by the user in response to the content are out of a predetermined range relative to the user's behavior and sound at the time of stability, determining that the user is in the state of tension, and the modifying further comprises, in response to determining that the person detected by the analysis processing makes the user feel psychological burden, changing, by a predetermined processing, an area of the person in the content by at least one of blurring or changing a color of a portion of the video output corresponding to the person.

2. The content output device according to claim 1, wherein the modifying further comprises controlling the audio output unit to convert or mute the sound of the person in the audio output.

3. The content output device of claim 2, wherein the controlling of the audio output unit comprises at least one of outputting a sound in an opposite phase of the sound of the person, changing a frequency of the sound of the person, converting the sound of the person to a second of another person, or changing the sound of the person to another sound.

4. The content output device according to claim 1, wherein the performing further comprises, in response to detecting that the person detected by the analysis process is speaking with a strong voice or has a yelling facial expression, identifying the person as a cause of the user's psychological burden.

5. A content output method performed in a content output device provided with a memory that is configured to store computer-executable instructions, and a processor that is configured to execute the computer-executable instructions, wherein the method comprises:

capturing, by a camera, an image of a user;

detecting, by a microphone, ambient sound including sound emitted from the user;

acquiring and rendering content as at least video output via a display unit and audio output via a sound output unit;

detecting a psychological state of a user in response to the content based on the biometric information which is detected by a biometric sensor and which includes at least one of heart rate, blood flow, blood pressure, body temperature, or brain waves;

storing psychological information indicating a psychological state when the user is in a state of tension in response to the content;

performing analysis processing on the content to identify, based on information on at least one of a sound of a person detected in the audio output by the analysis processing or a facial expression of the person detected in the video output by the analysis processing and the psychological information, a cause of burden included in the content and making the user feel a psychological burden; and modifying the content in a manner that changes an output method of the cause of burden, wherein the detecting of the psychological state of the user comprises:

detecting behavior of the user in response to the content from the image, detecting sound, obtained by the microphone, uttered by the user in response to the content, comparing the behavior of the user in response to the content and the sound uttered by the user in response to the content with user's behavior and sound at a time of stability, and in response to determining that the behavior of the user in response to the content and the sound uttered by the user in response to the content are out of a predetermined range relative to the user's behavior and sound at the time of stability, determining that the user is in the state of tension, and the modifying further comprises, in response to determining that the person detected by the analysis processing makes the user feel psychological burden, changing, by a predetermined processing, an area of the person in the content by at least one of blurring or changing a color of a portion of the video output corresponding to the person.

6. A non-transitory computer readable recording medium provided in a content output device provided with a memory that is configured to store computer-executable instructions, and a processor that is configured to execute the computer-executable instructions to perform operations, wherein the non-transitory computer-readable medium stores therein a computer program causing a computer to execute:

capturing an image of a user by a camera;

detecting ambient sound including sound emitted from the user by a microphone;

acquiring content;

rendering the content as video output on a display unit and audio output via a sound output unit;

detecting a psychological state of a user in response to the content based on the biometric information which is detected by a biometric sensor and which includes at least one of heart rate, blood flow, blood pressure, body temperature, or brain waves;

performing analysis processing on the content to identify, based on information on at least one of a sound of a person detected in the audio output by the analysis processing or a facial expression of the person detected in the video output by the analysis processing and the psychological information, a cause of burden included in the content and making the user feel a psychological burden; and modifying the content to change an output method of the cause of burden, wherein the detecting of the psychological state of the user comprises:

detecting behavior of the user in response to the content from the image, detecting sound uttered by the user in response to the content from the microphone, comparing the behavior of the user in response to the content and the sound uttered by the user in response to the content with user's behavior and sound at a time of stability, and based on a determination that the behavior of the user in response to the content and the sound uttered by the user in response to the content are out of a predetermined range, determining that the user is in the state of tension, and the modifying further comprises, in response to determining that the person detected by the analysis processing makes the user feel psychological burden, changing, by a predetermined processing, an area of the person in the content by at least one of blurring or changing a color of a portion of the video output corresponding to the person.

* * * * *